United States Patent [19]

Hennings et al.

[11] Patent Number: 4,711,526
[45] Date of Patent: Dec. 8, 1987

[54] ATTENUATING BEAM SPLITTER

[75] Inventors: David Hennings, El Granada; Nubar Manoukian, Cupertino, both of Calif.

[73] Assignee: Coherent, Inc., Palo Alto, Calif.

[21] Appl. No.: 882,485

[22] Filed: Jul. 7, 1986

[51] Int. Cl.⁴ .................... G02B 27/12; G02B 27/14
[52] U.S. Cl. ...................................... 350/170; 350/171
[58] Field of Search ............... 350/169, 170, 171, 173; 219/121 LT, 121 LU, 121 LV

[56] References Cited

U.S. PATENT DOCUMENTS

| | | | |
|---|---|---|---|
| 3,485,552 | 12/1969 | Adler | 350/160 |
| 4,035,070 | 7/1977 | Hammond | 355/3 |
| 4,362,361 | 12/1982 | Campbell et al. | 350/171 |
| 4,660,932 | 4/1987 | Eckbreth | 350/171 |

FOREIGN PATENT DOCUMENTS 52-5540  1/1977  Japan .

*Primary Examiner*—John K. Corbin
*Assistant Examiner*—Vincent J. Lemmo
*Attorney, Agent, or Firm*—Limbach, Limbach & Sutton

[57] ABSTRACT

An apparatus is disclosed for attenuating the beam of a laser. The apparatus is particularly suited for situations where a low powered aiming beam is necessary to be coaxially aligned with a full power working beam. The apparatus includes a refractive element having a pair of spaced-apart, parallel faces. A mounting arrangement is provided for selectively moving the refractive element into and out of the path of the full power laser beam. The refractive element is mounted such that when it is moved into the path of the laser beam, the beam will be split into primary and secondary beams. The primary beam will exit the refractive element along a path displaced from the incoming beam. The power of this exiting primary beam can be captured through a beam dump. The secondary beam is a product of at least two internal reflections within the refractive element. The secondary beam is highly attenuated and travels along the same path as the incoming beam. The secondary beam may be used for aiming since the full power beam will travel along the same path as the attenuated beam after the refractive element is moved out of its path.

13 Claims, 8 Drawing Figures

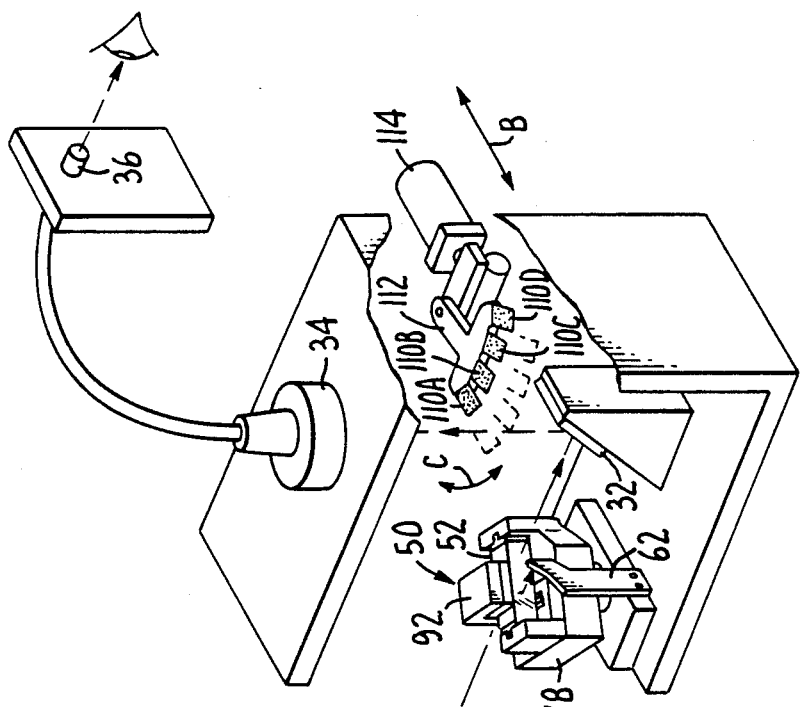
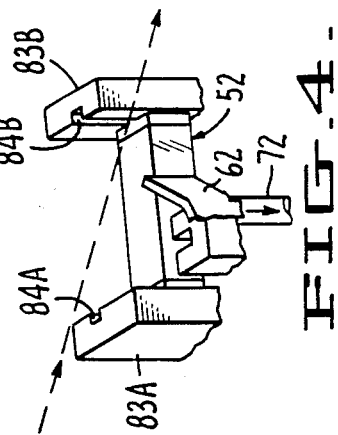
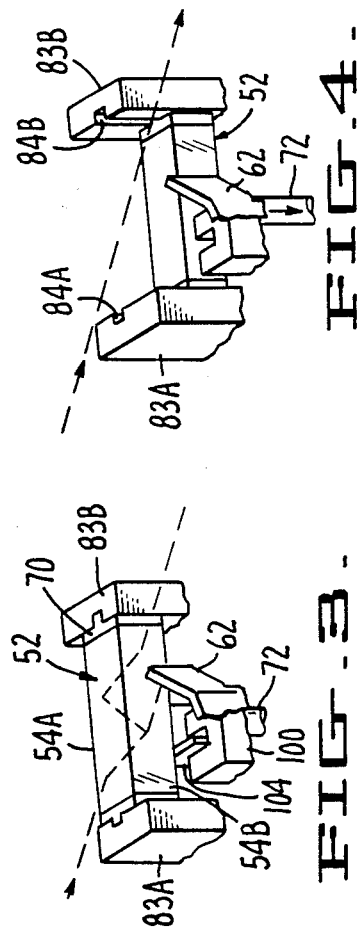
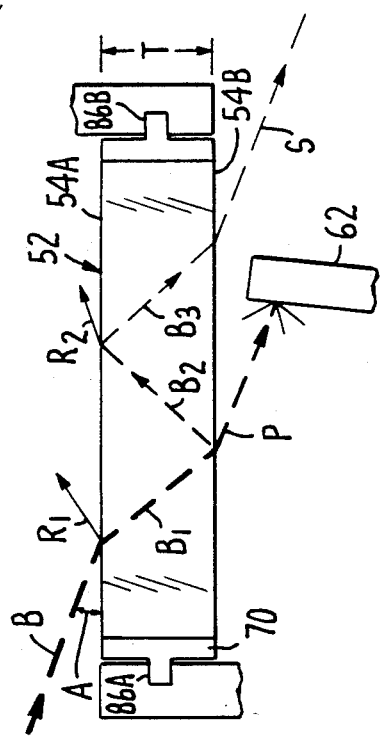

ATTENUATING BEAM SPLITTER

TECHNICAL FIELD

The subject invention relates to an apparatus for attenuating the power of a laser beam. The subject apparatus is particularly suited for use in surgical lasers where an attenuated version of the surgical beam is utilized for aiming the laser.

BACKGROUND OF THE INVENTION

For quite some time, the benefits of utilizing lasers for medical surgery have been recognized. For example, lasers are used by physicians to perform delicate operations within the eye of a patient. A laser is desirable because it can be used to treat very localized regions. More particularly, since laser light is coherent, it can be focused quite accurately. In addition, the absorption characteristics of tissues within the eye vary as a function of laser wavelength. Thus, particular features in the eye can be treated by choosing the proper wavelength radiation.

In all laser surgical devices, a means must be provided to permit the operator to aim the laser beam prior to treatment. Once the laser beam has been properly aimed, the high-powered surgical beam is activated. The time during which the surgical beam is actuated will typically be much shorter than the time necessary for aiming the beam. As can be appreciated, for surgery in delicate areas such as the eye, the aiming beam must have much less power than the surgical beam.

In some laser surgical devices, the laser generates wavelengths which are not visible to the human eye and therefore cannot be seen by the operator. In these devices, a second, low power laser which emits a visible beam is provided to generate an aiming beam. The use of a second laser to provide an aiming beam creates a number of problems. More specifically, optical elements must be provided to ensure that the aiming beam exits the device along a path coaxial with the surgical beam. In this manner, the operator can insure that the surgical beam will be delivered to the same location at which the aiming beam had been focused.

In many laser surgical devices, the surgical laser itself generates wavelengths that are visible to the human eye. In this case, it is preferable to use an attenuated version of the surgical beam to aim the laser. As can be appreciated, if the same laser is used to generate both the aiming and surgical beam, there is no need to align two different lasers. Accordingly, in prior art devices where only one laser is used, a variety of different approaches have been used to attenuate the power of the surgical beam such that a weakened, low power version of the beam can be used for aiming.

The simplest form of a beam attenuator would be a neutral density filter that is selectively placed into the path of the high power surgical laser beam. A neutral filter would tend to absorb a portion of the surgical beam prior to its reaching the patient. The latter approach, however, is unsatisfactory for present surgical lasers. More specifically, since a neutral density filter performs the attenuation function by absorbing light energy, heating will occur in the filter. If the surgical beam is relatively powerful, this absorption will create a rapid temperature rise in the filter, causing it to crack.

Accordingly, where higher power surgical lasers are utilized, attenuating filters have been designed which include a thin, dielectric film layer. The dielectric film layer is specifically designed to reflect a large portion of the beam hitting its surface. The reflected portion of the beam is then directed to a beam dump which can safely absorb the laser power. The portion of the laser beam which passes through the dielectric film is highly attenuated. The plane of the filter is placed perpendicular to the path of the laser such that the attenuated beam passing through filter travels along the same path as the incoming beam. By this arrangement, the attenuated beam can be readily used as the aiming beam. When the filter is removed from the path of the beam, the full powered surgical beam will be delivered to the treatment area.

A beam initially attenuated by a dielectric film filter can also be passed through a neutral density filter located downstream from the dielectric film filter to further attenuate the beam. Since the beam has already been significantly reduced in power by the dielectric film filter, a downstream neutral density filter can be used since rapid overheating will not occur.

In practice, a device can be provided with a plurality of downstream neutral density filters of different strengths. By preselecting one filter from this group, the power of the aiming beam reaching the patient's eye can be varied over a wide range. The ability to select different powers of the attenuated beam is desirable since the amount of penetration of the aiming beam is related to its power. For example, if the surgeon is operating on a relatively clear eye, a very low power aiming beam may be sufficient. However, if the interior of the eye is clouded, a much higher power aiming beam will be necessary to penetrate the eye. Even in the latter case, the most powerful aiming beam will still be at least one thousand times weaker than the surgical beam.

In the photocoagulators marketed by Coherent, Inc., the assignee of the subject invention, a combination of dielectric film reflectors and neutral density filters have been utilized. This approach was quite satisfactory where the photocoagulator had a single type of laser emitting radiation over a narrow range. In this case, dielectric filter elements could be designed relatively easily to reflect the proper amount of radiation.

As pointed out above, it has been recognized that various types of eye surgery can be performed with different laser wavelengths. Accordingly, photocoagulators have been marketed which have included more than one type of laser to increase the range of wavelengths available to the surgeon. One type of prior art photocoagulator utilized both an argon ion laser and a krypton ion laser. An argon ion laser will generate significant output lines at 488 and 514 nanometers, while a krypton ion laser will generate significant power at wavelengths of 531, 568, 647, and 676 nanometers.

About one and one-half years ago, Coherent, Inc., introduced a new photocoagulator which used a combination argon ion laser and a dye laser. In this device, the output lines from the argon ion laser could be used to perform surgery. In addition, the argon laser beam could also be redirected by the internal optics of the device to pump the cavity in a dye laser. In this orientation, the beam from the dye laser could then be used for surgery. One of the key advantages of a dye laser is that its output is tuneable over a relatively wide range of wavelengths. For example, the dye laser used in Coherent's present photocoagulator generates radiation across spectrum from 577 to 630 nanometers. Additional background information relating to this laser system and in particular, the optical elements suitable for redirecting the beam of an argon laser to the cavity of the dye laser can be found in copending application, Ser. No. 881,135, filed July 1, 1986, incorporated herein by reference.

The above described argon/dye laser photocoagulator provides the surgeon with great flexibility in selecting a suitable wavelength radiation for treatment. However, the ability to generate such a wide spectrum of laser wavelengths increased the difficulty of designing suitable attenuation optics. More particularly, it was found to be very difficult to design and manufacture dielectric film filters which had constant reflectance characteristics over the entire range of laser wavelengths.

Initially, a number of different dielectric film filters were selectively used during operation of the prior art argon/dye laser photocoagulator. In the meantime, efforts were made to develop a beam attenuator which would be operative over a wide range of wavelengths. The result of such efforts produced the attenuator of the subject invention. It should be noted that while the subject beam attenuator was designed specifically for an argon/dye photocoagulator, it can also be utilized in place of other attenuation optical elements found in prior art surgical devices.

Accordingly, it is an object of the subject invention to provide a new and improved apparatus for attenuating the power of a laser beam.

It is another object of the subject invention to provide a new and improved beam attenuator for use in a photocoagulator.

It is a further object of the subject invention to provide a new and improved apparatus which can be selectively placed in the path of a laser beam to produce an attenuated beam that travels along the same path as the incoming laser beam.

It is still another object of the subject invention to provide an apparatus which can be selectively moved into the path of a surgical laser beam in order to refract the main portion of the laser beam into a suitable beam dump.

SUMMARY OF THE INVENTION

In accordance with these and many other objects, the subject invention provides for an apparatus for selectively attenuating the power of a laser beam. The apparatus is particularly suitable for surgical devices where the attenuated beam must travel along the same path as the surgical beam.

The subject apparatus consists of a refractive element having a pair of spaced-apart, parallel faces. In the preferred embodiment, the refractive element is defined by a piece of quartz. A means is provided for moving the refractive element into and out of the path of the surgical laser beam.

The refractive element is mounted in a manner such that when it is out of the path of the surgical laser beam, the surgical laser beam will travel directly to the output of the photocoagulator. However, when the refractive element is placed in the path of the surgical beam, a large portion of the surgical beam will be refracted and exit the element along a path displaced from the incoming beam. A suitable beam dump can be placed along this alternate path for absorbing the energy of the surgical laser. In addition to the displaced beam, a highly attenuated portion of the beam will also be transmitted through the refractive element after a pair of internal reflections. By arranging the angle of the refractive element with respect to the incoming beam, this attenuated beam can be made to exit the element along the same path as the incoming beam.

This attenuated beam can then be used by the surgeon to aim the laser at the treatment area. To begin treatment, the refractive element is moved out of the path of the beam so that its full power is delivered to the proper location. When surgery is completed, the refractive element is moved back into place. As in the prior art, it is preferable to pass the attenuated aiming beam through one or more downstream neutral density filters to further attenuate and trim the power of the aiming beam.

Further objects and advantages of the subject invention will become apparent from the following detailed description taken in conjunction with the drawings, in which:

BRIEF DESCRIPTION OF THE DRAWINGS

FIG. 1 is a perspective view illustrating the main component parts of a combination argon and dye laser photocoagulator in which the subject attenuating beam splitter is utilized.

FIG. 2 is a top plan view of the refractive element of the attenuating beam splitter of the subject invention.

FIG. 3 is a perspective view of the refractive element and beam dump of the attenuating beam splitter of the subject invention.

FIG. 4 is a perspective view similar to FIG. 3, illustrating the refractive element lowered out of the path of the surgical beam.

DESCRIPTION OF THE PREFERRED EMBODIMENT

Figure 5:
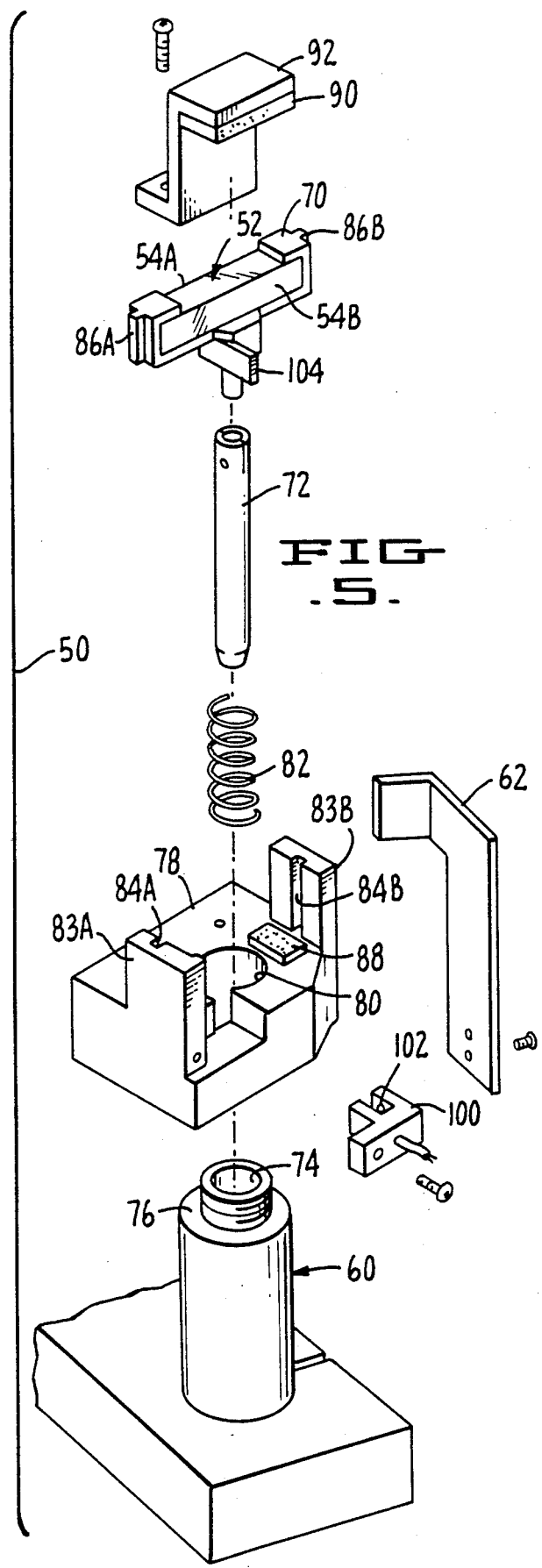
FIG. 5 is an exploded perspective view of the attenuating beam splitter of the subject invention.

Referring to FIG. 1, there is illustrated the main components of a combination argon and dye laser photocoagulator. Utilizing this apparatus, a surgeon can perform delicate eye surgery using the output beam of either the argon laser or a dye laser. The photocoagulator includes an argon laser 10 for emitting a beam 12. The argon laser can be of the type shown in U.S. Pat. No. 4,378,600, issued Mar. 29, 1983, and marketed by Coherent under the trademark "INNOVA".

The photocoagulator further includes an arrangement of fixed optical elements, in this case, mirrors 14A through 14E, for directing the argon beam to the optical cavity of the dye laser 15. The optical cavity of the dye laser is defined by high reflective mirror 16 and fold mirror 18 and output coupler 20. A pump system 22 is provided for circulating a fluid having an organic dye therein through the dye laser cavity in a non-colinear pump design as described in U.S. Pat. No. 3,873,946, assigned to Coherent, Inc. The optical energy in the argon beam functions to pump energy into the dye causing it to lase. The output of the dye is passed through a birefringent filter 24, which can be tuned to vary the output wavelength of the laser. A description of a birefringent filter can be found in U.S. Pat. No. 3,868,592, assigned to Coherent, Inc. The beam 30, which exits the dye laser 15, will then be reflected upwardly by a mirror 32 to a fiber optic input 34. The location of the fiber optic output 36 is controlled by the surgeon.

Where the argon beam 12 itself is to be utilized to perform surgery, a beam selector 38 is used to reroute the path of the argon beam 12 directly to mirror 32. In the illustrated embodiment, the beam selector is defined by a frame 40 which is pivotally mounted to a support 42. When the argon beam is to be used, the frame is pivoted to a downward position, as shown in phantom at 40A. In this position, the output beam of the argon laser strikes a first mirror 44 and is deflected to a second mirror (not shown) on the other side of the selector, where it is again redirected to the output mirror 32. The pivoting beam selector 38 provides an improved means for intercepting and redirecting a laser beam, and is the subject of assignee's copending application, Ser. No. 881,135, cited above.

As discussed above, in most laser surgical devices, it is necessary to provide a low power beam which travels along the same path as the surgical beam to facilitate aiming of the laser. Where the output of the surgical laser is visible to the human eye, it is preferable to create the aiming beam by attenuating the main beam. In the prior art, and in particular, applicant's earlier versions of the illustrated photocoagulator, the first order of attenuation was achieved using known dielectric film filters. Because of the wide spectrum of wavelengths which can be generated in the combination argon/dye laser system, it was found difficult to design suitable attenuation optics using dielectric film filters.

Accordingly, in the subject invention, a new and improved apparatus is provided for attenuating both the argon and dye laser beams. As illustrated in detail in FIGS. 5 through 8, the apparatus 50 includes a refractive element 52 having two parallel faces 54A and 54B. In a preferred embodiment, the refracting element is formed from a solid piece of quartz. Other materials may be suitable, but it is necessary that element 52 have a refractive index different from the medium (in this case, air) in which the incoming laser beam is travelling. For example, the refractive element 52 can be made up of two plates of one material and a center body of another material. It is also necessary that two faces 54A and 54B be parallel to achieve the optical results discussed in detail below.

In accordance with the subject invention, a means is provided for moving refractive element 52 into and out of the path of the laser beam. In the illustrated embodiment, this means is defined by an electric solenoid motor, shown generally as 60, which will also be described in greater detail below.

Turning back to FIGS. 2 through 4, the operation of the refractive element 52 will first be discussed. FIGS. 2 and 3 illustrate the situation where the refractive element 52 is located in the raised position, in the path of the surgical laser beam B. FIG. 4 illustrates the situation where the refractive element 52 is lowered out of the path of beam B such that the full power of the beam may be directed to the treatment area. In these figures, the incoming laser beam is referred to as "B" since it could represent either the dye laser beam 30 or the argon laser beam 12. In fact, since the subject invention may be used in any device where an attenuated aiming beam is desired, FIGS. 2 and 3 may be thought of as a generic illustration not limited to the argon/dye laser combination.

As illustrated in FIG. 2, when the main beam B enters element 52, it is refracted at face 54A. As can be appreciated, a small portion of the beam B (shown as ray $R_1$) will also be reflected off the surface 54A and never enter the element 52. The majority of beam B, however, will pass through element 52 (shown as $B_1$) and be refracted once again as it passes through face 54B. The exiting main beam, hereinafter referred to as the primary beam P, passes out of element 52 along a path parallel to the original beam B but displaced therefrom. Primary beam P may be captured by a suitable beam dump 62 which is designed to dissipate heat rapidly.

As illustrated in FIG. 2, when beam $B_1$ strikes face 54B, a small portion (shown as ray $B_2$) will be reflected internally back towards face 54A. At face 54A, a portion of the beam will exit element 52 (shown as ray $R_2$) and another portion will be internally reflected, shown as beam $B_3$. When beam $B_3$ reaches face 54B, a portion will be refracted and exit along the path shown by beam S. Beam S or the secondary beam will be highly attenuated with respect to incoming beam B. More importantly, secondary beam S travels out of the element 52 along the same path as incoming beam B. The latter result is important since the surgeon must know that when element 52 is lowered, the surgical beam B will be delivered to the same spot as the aiming beam.

In order to achieve this result, faces 54A and 54B of element 52 must be parallel. In addition, the angle A, between the incoming beam B and face 54A must be properly adjusted. This angle A is a function of the refracting power of element 52 which is, in turn, a function of the wavelength of incoming beam B. The angular adjustment of element 52 can be made empirically by marking the location at which the surgical B will be delivered by the optic output 36 when the refracting element is located out of the path of the beam. The element is then placed into the path of the beam. The angle of the element 52 can then be varied until the secondary beam S is delivered to the same spot as the main beam. In the illustrated photocoagulator, where quartz is used as the refractive element 52 and the wavelengths to be attenuated range from 488 to 630 nanometers, a suitable value for angle A is on the order of 22 degrees.

If element 52 was mounted in a manner such that secondary beam S did not travel along the same path as incoming beam B, this deviation might be correctable with a second optical element, such as a prism. In this case, both the refractive element and the correcting prism would have to synchronously moved out of the path of beam B during treatment. For this reason, it is preferable to arrange refractive element 52 in the manner described above so that only a single element need be moved. However, it is intended that the scope of the subject invention include an arrangement wherein the refracting element includes a correcting optical element.

The level of attenuation of the secondary beam S with respect to incoming beam B depends on a number of factors. For example, the clarity or pureness of the quartz will effect the level of attenuation. Another factor which will affect the level of attenuation of secondary beam S is the polarization angle of the incoming laser beam B. More specifically, if beam B is vertically polarized, less light will pass through element 52 than if the beam is polarized in the horizontal plane. In the preferred embodiment, the beam is polarized vertically.

Another important factor in determining the attenuation level of secondary beam S is the reflectivity of the opposing faces 54A and 54B with respect to the laser beam. If these faces are highly transparent to the beam, the power of the primary beam P will be maximized and only a small portion of the beam energy will be available to create secondary beam S. In the embodiment incorporated in the Coherent's 900 series photocoagulator, the attenuation factor of element 52 is on the order of 50 to 1, that is, the power of secondary beam S will be 1/50 of the power of the incoming beam B.

In the preferred embodiment, the thickness T of element 52 is 6.4 mm. If element 52 is made thicker, the separation or displacement between outgoing beams P and S can be increased. As the displacement is increased, it becomes easier to capture and dissipate the power of primary beam P. Unfortunately, as the thickness of element 52 is increased, its weight will also be increased. In operation, it is desirable that element 52 be rapidly moved into and out of the path of beam B. Thus, if the thickness of element 52 is reduced and its weight is lessened, it may be moved into and out of the path of beam B faster. Another factor tending towards reducing the thickness of element 52 is the fact that a higher optical quality can be maintained with less material. Therefore, the thickness T of element 52 should only be large enough to insure that primary beam P can be fully captured.

Referring back to FIGS. 5 through 8, the means for mounting and for moving element 52 will be described in greater detail. In the preferred embodiment, element 52 is mounted in a generally U-shaped bracket 70. Bracket 70 is connected to a cylindrical rod 72 formed from a conductive material. Rod 72 received in the cylindrical opening 74 of solenoid 60. Mounted to the upper surface or shelf 76 of solenoid 60 is a platform 78 having a central aperture 80 through which rod 72 can pass.

A spring 82 is mounted about rod 72 and abuts shelf 76 of solenoid 60. Spring 82 is provided to bias element 52 towards its upward position, in the path of the beam. In this location, the beam B will be attenuated and not capable of destroying human tissue.

Platform 78 includes a pair of upstanding arms 83A and 83B. Each arm includes a channel 84A and 84B for receiving a pair of flanges 86A and 86B provided on the opposed sides of U-shaped bracket 70. Flanges 86 ride in channels 84 to guide element 52 up and down during operation. Preferably, a pair of resilient pads 88 are provided on platform 78 to cushion the downward movement of element 52. Similarly, an upper pad 90 is attached to bracket 92 which is mounted to platform 78. Upper pad 90 provides a resilient stop to reduce the chance of damage to element 52 when it is biased back into its upper position.

As discussed earlier with reference to FIG. 2, a beam dump 62 is provided for absorbing the power of the refracted primary beam P. Dump 62 is defined by a bracket mounted to platform 78. Beam dump 62 is made from black anodized aluminum and is designed to rapidly conduct heat generated by the primary beam P down through the frame of the device. As discussed above, some of the power of beam B will also be reflected back off surface 54A as ray $R_1$, and additional energy will escape as ray $R_2$. If these rays have significant power, additional beam dumps can be provided. In the preferred embodiment, bracket 92 also acts as the beam dump for rays $R_1$ and $R_2$.

When the solenoid 60 is not activated, spring 82 functions to bias element 52 into the upward position shown in FIGS. 1 through 3. When solenoid 60 is energized, the cylindrical rod 72 will be drawn downwardly into opening 74 pulling element 52 out of the path of the beam and allowing its full power to be delivered to the fiber optic input 34 of the photocoagulator.

In the commercial embodiment, the activation of the solenoid is typically controlled by a foot pedal. The surgeon will preset the desired treatment time on a control panel. When the foot pedal is pressed, a voltage will be supplied to the solenoid and maintained until the set time period elapses. The voltage will then be terminated, allowing the element to move back to the upward position.

Figure 6:
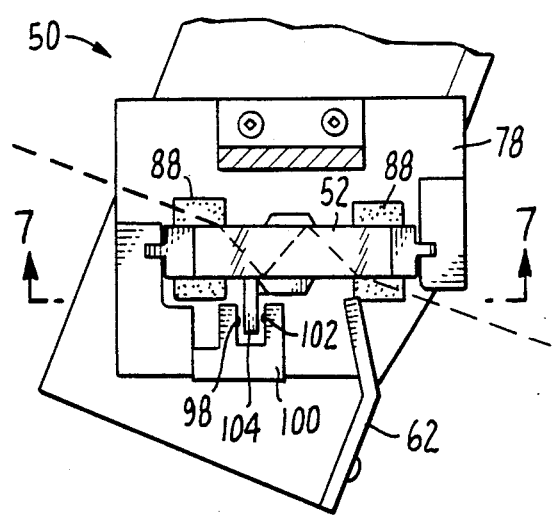
FIG. 6 is a top plan view, with parts removed for clarity, of the attenuating beam splitter of the subject invention.
Figure 7:
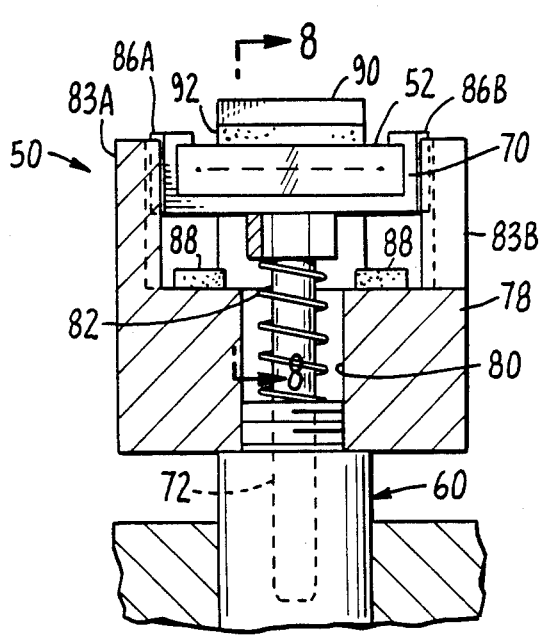
FIG. 7 is a cross-sectional view taken along the line 7—7 of FIG. 6 of the attenuating beam splitter of the subject invention.
Figure 8:
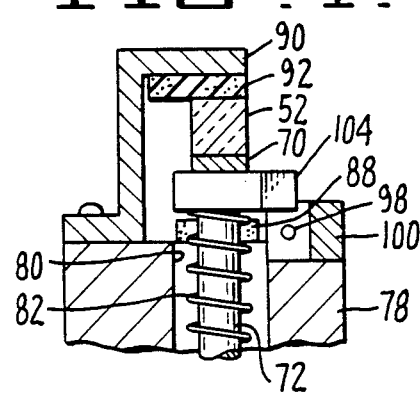
FIG. 8 is a partial cross-sectional view, taken along the lines 8—8 of FIG. 7, illustrating the attenuating beam splitter of the subject invention.

Because of the potential damaging results which could occur if element 52 failed to properly return to its upper position, a sensing means may be provided to indicate the position of the element. In the illustrated embodiment, a sensor 98 is affixed to platform 78 via a bracket 100. Sensor 98 consists of an LED and photodetector combination which is mounted in a channel 102 formed in bracket 100. Bracket 70 includes a complimentary projecting flange 104 which is receivable in channel 102 as shown in FIGS. 3 and 6. In this position, the light from the diode is blocked from the photodetector indicating that element 52 is out of the path of beam B. When the element 52 is in the upward position, flange 104 will be located out of the path of sensor 98 (as seen in FIG. 8) and a suitable signal will be generated and detected. If, however, the solenoid has been electrically deactivated and the expected signal is not generated, it would indicate that element 52 has not been biased back to the upward position attenuating beam B. In this case, other safety measures can be taken, including shutting down the laser itself or swinging a beam dump (not shown) into the path of the laser.

As pointed out above, refractive element 52 functions to attenuate the main beam by a fixed amount. In practice, it is desirable to provide the surgeon with an aiming beam of various powers. Accordingly, a plurality of trimming filters may be utilized to further attenuate the beam. Trimming filters have been used in Coherent's 900 series photocoagulators and, therefore, need not be described in detail. As illustrated in FIG. 1, four neutral density filters 110A through 110D are mounted on a pallet-like device 112. Pallet 112 is in turn connected to a solenoid 114. The solenoid functions to translate pallet 112 in the direction as shown by arrow B, and in addition, to rotate the pallet 112 about an axis as shown by arrow C. In this manner, any one of the filters 110A through D can be moved into the path of secondary beam S.

Filters 110 A-D are neutral density filters of varying strength. As discussed above, it is possible to use neutral density filters at this stage for further attenuation since the power of the beam S is relatively low and therefore the danger of overheating and cracking of the filter due to absorbed energy is eliminated. In the preferred embodiment filters 110A through 110D, in combination with the refractive element produce a final attenuation of the secondary beam S with respect to the incoming beam B that ranges approximately from $10^3:1$ to $10^5:1$.

In operation of the device, the surgeon will select which laser beam (argon or dye) will be used for treatment. In either case, one of the laser beams 12 or 30 will be directed through the refractive element 52 of the attenuator 50 of the subject invention. In addition, one of the neutral density filters will also be selected. If the surgeon wishes to have an extremely low power aiming beam, a higher density filter 110 will be used. In contrast, if more power is required of the aiming beam, a lower density 110 filter will be used.

The surgeon will aim the secondary beam S so that it is focused on the area to be treated. The surgeon will then operate a switch which will energize solenoid 60, pulling the refractive element 52 downwards and out of the path of beam B. At the same time, the neutral density filter 110 will be pulled out of the path of beam B. The full power beam B will then travel along the same path as the attenuated beam S and treat the patient. When the treatment time has elapsed, solenoid 60 will be deenergized and the refractive element 52 will be biased back to its upward position by spring 82 attenuating the beam.

In summary, there has been provided a new and improved apparatus for attenuating the beam of a laser. The apparatus includes a refractive element 52 having a pair of spaced-apart, parallel faces 54A and B. A means is provided for selectively moving the refractive element 52 into and out of the path of the laser beam. The refractive element is mounted in such a manner that when it is placed into the path of the laser beam, the incoming beam will be split into primary and secondary beams. The primary beam will exit the refractive element along a path parallel to, but spaced from, the incoming laser beam. In this manner, most of the power of the beam can be captured. The secondary beam exits the refractive element after at least a pair of internal reflections and is therefore highly attenuated. In accordance with the subject invention, the secondary beam travels along the same path as the primary beam such that it can be used for aiming.

While the subject invention has been described with reference to a preferred embodiment, various changes and modifications could be made therein, by one skilled in the art, without varying from the scope and spirit of the subject invention as defined by the appended claims. For example, in the illustrated embodiment, the secondary beam is shown as being produced after only two internal reflections. It will be appreciated that a number of parallel attenuated beams will be produced as a result of multiple internal reflections. Any one of these attenuated beams could be used as the aiming beam as long as it is made to travel along the same path as the incoming beam.

We claim:

1. An apparatus for attenuating the power of a laser beam comprising a refractive element having a pair of spaced-apart, parallel faces, said element being at least partially transmissive to said laser beam and located such that when said laser beam enters said refractive element through one of said faces, said laser beam will be split into at least a primary laser beam and a secondary laser beam both of which exit said refractive element out of the other of said faces, with said primary laser beam exiting said refractive element along a path displaced from the incoming laser beam, and with the secondary laser beam exiting said refractive element after undergoing at least two internal reflections, with the power of the secondary laser beam being attenuated with respect to the incoming laser beam and with the secondary laser beam travelling along the same path as the incoming laser beam.

2. An apparatus as recited in claim 1 further including a beam dump located in a manner to absorb the power from said exiting primary laser beam.

3. An apparatus as recited in claim 1 where said refractive element is formed from quartz.

4. An apparatus as recited in claim 1 wherein said refractive element is substantially transparent.

5. An apparatus as recited in claim 1 wherein said refractive element is mounted with respect to the incoming laser beam at an angle on the order of 22 degrees.

6. In a device including a laser emitting a beam of radiation, an apparatus for selectively attenuating the power of said laser beam comprising:
   a refractive element having a pair of spaced-apart, parallel faces, said element being at least partially transmissive to said laser beam;
   means for moving said refractive element into and out of the path of said laser beam; and
   mounting means for supporting said refractive element in a manner such that when said refractive element is placed into the path of said laser beam by said moving means, said laser beam will enter said refractive element through one of said faces and be split into at least a primary laser beam and a secondary laser beam both of which exit said refractive element out of the other of said faces, with said primary laser beam exiting said refractive element along a path displaced from the incoming laser beam, and with the secondary laser beam exiting said refractive element after undergoing at least two internal reflections, with the power of the secondary laser beam being attenuated with respect to the incoming laser beam and with the secondary laser beam travelling along the same path as the incoming laser beam.

7. An apparatus as recited in claim 6 further including a beam dump located in a manner to absorb the power from said exiting primary laser beam.

8. An apparatus as recited in claim 6 where said refractive element is formed from quartz.

9. An apparatus as recited in claim 6 wherein said refractive element is substantially transparent.

10. An apparatus as recited in claim 6 wherein said refractive element is mounted with respect to the incoming laser beam at an angle on the order of 22 degrees.

11. An apparatus as recited in claim 6 wherein said means for moving said refractive element includes a solenoid.

12. An apparatus as recited in claim 6 further including a means for detecting the position of said refractive element.

13. An apparatus as recited in claim 12 wherein said means for detecting the position of said refractive element includes a light-emitting diode and sensor combination.

* * * * *